(12) United States Patent
Yu et al.

(10) Patent No.: US 10,082,593 B2
(45) Date of Patent: Sep. 25, 2018

(54) METHOD AND APPARATUS FOR SYNTHETIC MAGNETIC SENSOR APERTURE USING EDDY CURRENT TIME TRANSIENT MEASUREMENT FOR DOWNHOLE APPLICATIONS

(71) Applicant: GOWell International, LLC, Houston, TX (US)

(72) Inventors: Yanxiang Yu, Houston, TX (US); Jinsong Zhao, Houston, TX (US); Qinshan Yang, Katy, TX (US)

(73) Assignee: GOWell International, LLC, Houston, TX (US)

( * ) Notice: Subject to any disclaimer, the term of this patent is extended or adjusted under 35 U.S.C. 154(b) by 0 days.

(21) Appl. No.: 15/057,702

(22) Filed: Mar. 1, 2016

(65) Prior Publication Data

US 2017/0254916 A1 Sep. 7, 2017

(51) Int. Cl.
| | |
|---|---|
| *G01V 3/28* | (2006.01) |
| *E21B 17/10* | (2006.01) |
| *E21B 47/00* | (2012.01) |
| *E21B 47/12* | (2012.01) |
| *G01B 7/06* | (2006.01) |

(52) U.S. Cl.
CPC ............ *G01V 3/28* (2013.01); *E21B 17/1078* (2013.01); *E21B 47/0002* (2013.01); *E21B 47/12* (2013.01); *G01B 7/10* (2013.01)

(58) Field of Classification Search
CPC .............. G01V 3/00–3/40; G01B 7/00–7/345
See application file for complete search history.

(56) References Cited

U.S. PATENT DOCUMENTS

| | | | | |
|---|---|---|---|---|
| 5,753,813 A * | 5/1998 | Hagiwara | ............... | E21B 47/09 166/254.2 |
| 5,987,385 A * | 11/1999 | Varsamis | ............ | E21B 47/0002 702/6 |
| 6,907,597 B1 * | 6/2005 | Mamona | ............. | G06F 9/44505 712/1 |
| 7,884,611 B1 * | 2/2011 | Hall | ......................... | G01V 3/28 324/339 |
| 2005/0044344 A1 * | 2/2005 | Stevens | ............... | G06F 15/7867 712/227 |
| 2005/0088180 A1 * | 4/2005 | Flanagan | ............... | G01V 13/00 324/338 |
| 2006/0164092 A1 * | 7/2006 | Forgang | .................. | G01V 3/28 324/339 |
| 2006/0208737 A1 * | 9/2006 | Merchant | ................. | G01V 3/28 324/330 |
| 2007/0163348 A1 * | 7/2007 | Heckel | ................. | G01N 29/069 73/584 |

(Continued)

*Primary Examiner* — Tung X Nguyen
*Assistant Examiner* — David Frederiksen

(57) ABSTRACT

A method of creating a synthetic aperture. The method may comprise identifying a static configuration, inputting the static configuration into a dynamic controller, configuring a transmitter with the dynamic controller, and configuring a receiver with the dynamic controller. The method may further comprise inputting operational variables and environmental variables into a dynamic configuration, inputting the dynamic configuration into the dynamic controller, and re-configuring the transmitter and the receiver with the dynamic controller.

15 Claims, 7 Drawing Sheets

(56) References Cited

U.S. PATENT DOCUMENTS

| | | | | |
|---|---|---|---|---|
| 2008/0027311 | A1* | 1/2008 | Anderson | A61B 5/062 600/424 |
| 2008/0060497 | A1* | 3/2008 | Lambert | B60K 28/02 84/307 |
| 2008/0077382 | A1* | 3/2008 | Strehl | G06F 17/5022 703/20 |
| 2009/0230968 | A1* | 9/2009 | Bittar | E21B 47/024 324/338 |
| 2010/0102986 | A1* | 4/2010 | Benischek | E21B 47/121 340/855.8 |
| 2012/0109611 | A1* | 5/2012 | Loizzo | E21B 41/0064 703/10 |
| 2015/0219601 | A1* | 8/2015 | Davydov | E21B 47/00 324/229 |
| 2015/0311725 | A1* | 10/2015 | Yamamoto | G01V 3/104 307/104 |
| 2016/0168975 | A1* | 6/2016 | Donderici | E21B 47/0006 324/238 |
| 2016/0299248 | A1* | 10/2016 | Wu | E21B 47/00 |

\* cited by examiner

METHOD AND APPARATUS FOR SYNTHETIC MAGNETIC SENSOR APERTURE USING EDDY CURRENT TIME TRANSIENT MEASUREMENT FOR DOWNHOLE APPLICATIONS

CROSS-REFERENCE TO RELATED APPLICATIONS

Not applicable.

STATEMENT REGARDING FEDERALLY SPONSORED RESEARCH OR DEVELOPMENT

Not applicable.

BACKGROUND OF THE INVENTION

Field of the Invention

This invention relates to a field for imaging wall thickness variations, changes in tubing, imaging casing through a tube, and imaging multiple tubes using non-destructive means in cased-hole downhole logging applications. The changes and variations of tubing walls may be caused by internal and/or external patches, clamps, corrosions, errosions, and/or any combination thereof.

Background of the Invention

Tubing may be used in many different applications and may transport many types of fluids. Tubes may be conventionally placed underground and/or positioned in an inaccessible area, making inspection of changes within tubing difficult. It may be beneficial to measure the thickness variations within a tube while the tube is in use. Previous methods for inspecting tubes have come in the form of non-destructive inspection tools such as electromagnetic devices that may measure magnetic flux-leakage within tubing, which may not be able to detect changes in multi-pipe situations. Additionally, previous methods may not be able to perform multi-pipe azimuthal imaging. Electromagnetic devices may be well suited for tube inspection because they may operate and may be insensitive to any fluid within the tube.

Previous devices and methods that may measure flux-leakage may only be useful for the detection of localized damage in ferromagnetic pipes. The measurement of flux-leakage may be hindered by the type of tube, thinning of tubing, requirements of a strong magnetic field, strong flux coupling, and a requirement for the device to be in close proximity to the tube walls. Additionally, electromagnetic tools that use eddy-current may be better suited for measuring the integrity of tubing. Drawbacks of a constant eddy-current electromagnetic tool may be that the signal from several frequencies may not penetrate a first wall of tubing and allow inspection of the integrity of a second wall of a larger surrounding tubing. Transient electromagnetic methods using pulsed electromagnetic waves may be limited to increasing the signals from a second tube wall to additional tube walls, have problems optimizing a receiver coil, and may suffer Signal-to-Noise Ratio problems.

Consequently, there is a need for an electromagnetic tool which may induce a larger amount of eddy-current within surrounding pipe walls. In downhole applications, multi-piping wall variation imaging detection capability that may be accurate and efficient may be in high demand.

BRIEF SUMMARY OF SOME OF THE PREFERRED EMBODIMENTS

These and other needs in the art may be addressed in embodiments by a method for inspecting a tube. A method of creating a synthetic aperture. The method may comprise identifying a static configuration, inputting the static configuration into a dynamic controller, configuring a transmitter with the dynamic controller, and configuring a receiver with the dynamic controller. The method may further comprise inputting operational variables and environmental variables into a dynamic configuration, inputting the dynamic configuration into the dynamic controller, and re-configuring the transmitter and the receiver with the dynamic controller.

The foregoing has outlined rather broadly the features and technical advantages of the present invention in order that the detailed description of the invention that follows may be better understood. Additional features and advantages of the invention will be described hereinafter that form the subject of the claims of the invention. It should be appreciated by those skilled in the art that the conception and the specific embodiments disclosed may be readily utilized as a basis for modifying or designing other embodiments for carrying out the same purposes of the present invention. It should also be realized by those skilled in the art that such equivalent embodiments do not depart from the spirit and scope of the invention as set forth in the appended claims.

BRIEF DESCRIPTION OF THE DRAWINGS

For a detailed description of the preferred embodiments of the invention, reference will now be made to the accompanying drawings in which.

DETAILED DESCRIPTION OF THE PREFERRED EMBODIMENTS

The present disclosure relates to embodiments of a device and method for inspecting and detecting characteristics of tubing and devices attached to tubing. More particularly, embodiments of a device and method are disclosed for inspecting a number of tube walls surrounding an innermost tube wall. In embodiments, an inspection device may induce an eddy current in surrounding tube walls by producing an electro-magnetic field, wherein the induced eddy current may be recorded and analyzed for aberrations. Eddy currents may be produced by a sensor array, which may be switched on and off to produce and record an induced eddy current in a tube and/or surrounding tube walls. The eddy current decay and diffusion in the tube walls may be recorded, specifically recording voltage in embodiments, which may produce a function of the tube thickness and electromagnetic properties (e.g. metal conductivity and magnetic permeability) and the configurations of tubes. In embodiments, the power provided to different sensors may be the same and/or different. Manipulation of the configuration of ferri-cores may manipulate the transmission and direction of the electro-magnetic field.

In embodiments, an inspection device may be a magnetic sensor array with one or more cores, partially and/or fully wound by different number of transmitters and/or receivers. Windings disposed on transmitters and/or receivers may be in any shape and may comprise any number of turns. Further, transmitter coils and/or receiver coils may be disposed and wound on a sensor and/or multi sensors, in which the number of turns may be varied on any portion on the sensor.

In embodiments, the electro-magnetic field may be generated by a transmitter with any suitable shape and any suitable aperture. The receiver may receive signals with any suitable shape and any suitable aperture. A synthetic aperture produced and recorded by a transmitter and a receiver, respectively, may measure tubing thickness by adaptively controlling the logging speed and vertical resolution, which may decrease motion jitter effect of a downhole logging device.

Figure 1:
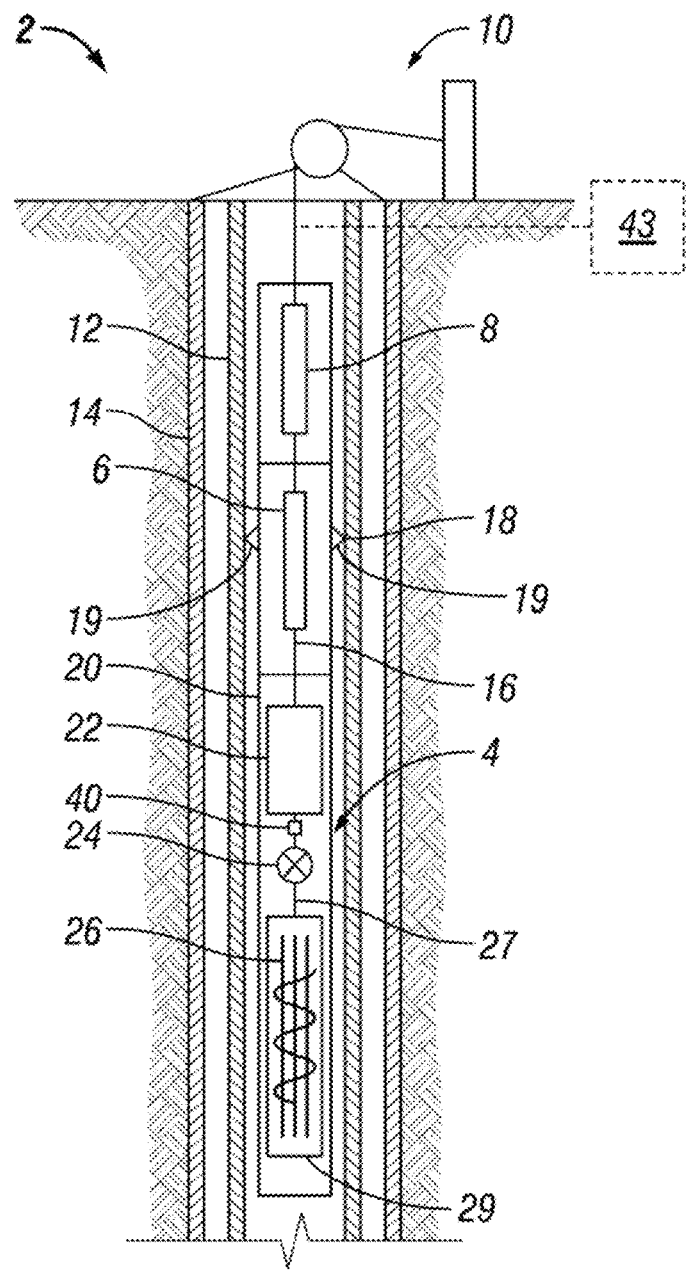
FIG. 1 illustrates an embodiment of an inspection system disposed downhole.

FIG. 1 illustrates an inspection system 2 comprising an inspection device 4, a centralizing module 6, a telemetry module 8, and a service device 10. In embodiments, inspection device 4 may be inserted into tubing 12, wherein tubing 12 may be contained within casing 14. In further embodiments, not illustrated, there may be a plurality of tubing 12, wherein an inner tube may be contained by several additional tubes. In embodiments, as shown, inspection device 4 may be disposed below centralizing module 6 and telemetry module 8. In other embodiments, not illustrated, inspection device 4 may be disposed above and/or between centralizing module 6 and telemetry module 8. In embodiments, inspection device 4, centralizing module 6, and telemetry module 8 may be connected to tether 16. Tether 16 may be any suitable cable that may support inspection device 4, centralizing module 6, and telemetry module 8. A suitable cable may be steel wire, steel chain, braided wire, metal conduit, plastic conduit, ceramic conduit, and/or the like. A communication line, not illustrated, may be disposed within tether 16 and connect inspection device 4, centralizing module 6, and telemetry module 8 with service device 10. Without limitation, inspection system 2 may allow operators on the surface to review recorded data in real time from inspection device 4, centralizing module 6, and telemetry module 8.

As illustrated in FIG. 1, service device 10 may comprise a mobile platform (i.e. a truck) or stationary platform (i.e. a rig), which may be used to lower and raise inspection system 2. In embodiments, service device 10 may be attached to inspection system 2 by tether 16. Service device 10 may comprise any suitable equipment which may lower and/or raise inspection system 2 at a set or variable speed, which may be chosen by an operator. The movement of inspection system 2 may be monitored and recorded by telemetry module 8.

Telemetry module 8, as illustrated in FIG. 1, may comprise any devices and processes for making, collecting, and/or transmitting measurements. For instance, telemetry module 8 may comprise an accelerator, gyro, and the like. In embodiments, telemetry module 8 may operate to indicate where inspection system 2 may be disposed within tubing 12 and the orientation of sensor array 26. Telemetry module 8 may be disposed at any location above, below, and/or between centralizing module 6 and inspection device 4. In embodiments, telemetry module 8 may send information through the communication line in tether 16 to a remote location such as a receiver or an operator in real time, which may allow an operator to know where inspection system 2 may be located within tubing 12. In embodiments, telemetry module 8 may be centered about laterally in tubing 12.

As illustrated in FIG. 1, centralizing module 6 may be used to position inspection device 4 and/or telemetry module 8 inside tubing 12. In embodiments, centralizing module 6 laterally positions inspection device 4 and/or telemetry module 8 at about a center of tubing 12. Centralizing module 6 may be disposed at any location above and/or below telemetry module 8 and/or inspection device 4. In embodiments, centralizing module 6 may be disposed above inspection device 4 and below telemetry module 8. Centralizing module 6 may comprise arms 18. In embodiments, there may be a plurality of arms 18 that may be disposed at any location along the exterior of centralizing module 6. Specifically, arms 18 may be disposed on the exterior of centralizing module 6. In an embodiment, as shown, at least one arm 18 may be disposed on opposing lateral sides of centralizing module 6. Additionally, there may be at least three arms 18 disposed on the outside of centralizing module 6. Arms 18 may be moveable at about the connection with centralizing module 6, which may allow the body of arm 18 to be move closer and farther away from centralizing module 6. Arms 18 may comprise any suitable material. Suitable material may be but is not limited to, stainless steel, titanium, metal, plastic, rubber, neoprene, and/or any combination thereof. In embodiments, the addition of springs 19 may further make up and/or be incorporated into centralizing module 6. Springs 19 may assist arms 18 in moving centralizing module 6 away from tubing 12, and thus inspection device 4 and telemetry module 8, to about the lateral center of tubing 12. Without limitation, centering inspection device 4 may produce more reliable and accurate voltage readings of tubing 12.

Inspection device 4, as illustrated in FIG. 1, may be located below centralizing module 6 and/or telemetry module 8. Inspection device 4 may be designed to detect defects and measure wall thickness in tubing 12 and surrounding tubing. In embodiments, inspection device 4 may be able to detect, locate transverse and longitudinal defects (both internal and external), determine the deviation of the wall thickness from its nominal value thorough the interpretation of voltage data. Tubing 12 may be made of any suitable material for use in a wellbore. Suitable material may be, but is not limited to, metal, plastic, and/or any combination thereof. Additionally, any type of fluid may be contained within tubing 12 such as without limitation, water, hydrocarbons, and the like. In embodiments, there may be additional tubing which may encompass tubing 12. Inspection device 4 may comprise a housing 20, a memory module 22, a transmitter and receiver controller 24, and a sensory array 26. Housing 20 may be any suitable length in which to protect and house the components of inspection device 4. In embodiments, housing 20 may be made of any suitable material to resist corrosion and/or deterioration from a fluid.

Suitable material may be, but is not limited to, titanium, stainless steel, plastic, and/or any combination thereof. Housing 20 may be any suitable length in which to properly house the components of inspection device 4. A suitable length may be about one foot to about ten feet, about four feet to about eight feet, about five feet to about eight feet, or about three feet to about six feet. Additionally, housing 20 may have any suitable width. The width may include a diameter from about one foot to about three feet, about one inch to about three inches, about three inches to about six inches, about four inches to about eight inches, about six inches to about one foot, or about six inches to about two feet. Housing 20 may protect memory module 22, a transmitter and receiver controller 24, and sensory array 26 from the surrounding downhole environment within tubing 12.

As illustrated in FIG. 1, memory module 22 may be disposed within inspection device 4. In embodiments, memory module 22 may store all received, recorded and measured data and may transmit the data in real time through a communication line in tether 16 to a remote location such as an operator on the surface. Memory module 22 may comprise flash chips and/or ram chips, which may be used to store data and/or buffer data communication. Additionally, memory module 22 may further comprise a transmitter, processing unit and/or a microcontroller. In embodiments, memory module 22 may be removed from inspection device 4 for further processing. Memory module 22 may be disposed within any suitable location of housing 20 such as about the top, about the bottom, or about the center of housing 20. In embodiments, memory module 22 may be in communication with differential amplifier 24 and sensor array 26 by any suitable means such as by a connection to differential amplifier 24 and sensor array 26 by a communication line 27. Memory module 22 may record voltage recordings transmitted from differential amplifier 24.

Transmitter and receiver controller 24, as illustrated in FIG. 1, may control the amplitude and phase of transmitter coils, amplifier factor, and signal acquiring period of receiver coils. Transmitter and receiver controller 24 may be pre-configured at the surface with certain logging environment and a logging case, which may be defined as static configuration, discussed below. It may also be dynamically configured by what a receiver may record. Transmitter and receiver controller 24 may be disposed at any suitable location within housing 20. In embodiments, such disposition may be about the top, about the bottom, or about the center of housing 20.

Figure 2:
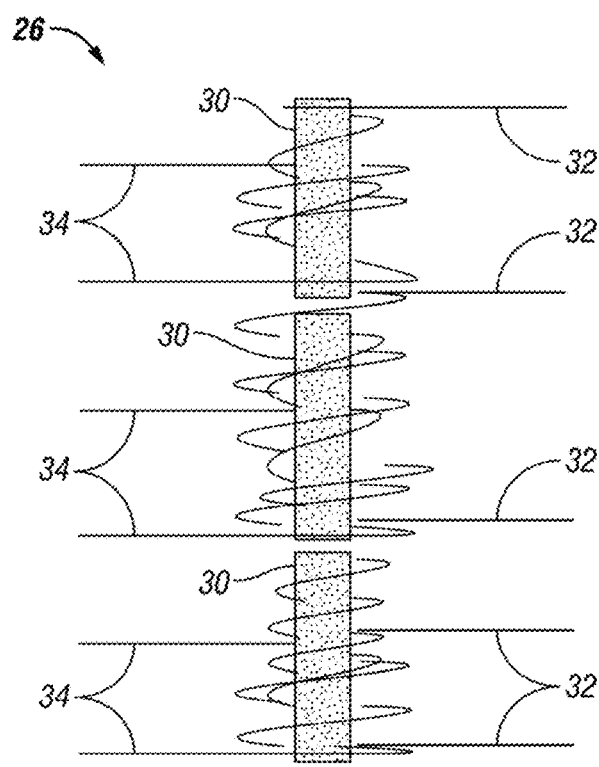
FIG. 2 illustrates an embodiment of a sensor array.

As illustrated in FIGS. 1 and 2, sensor array 26 may create an electro-magnetic field, which may induce an eddy current in surrounding tubing 12. The voltage charge within tubing 12, from the induced eddy current, may be sensed and recorded by sensor array 26. In embodiments, the recorded voltage may allow identification of the characteristics of tubing 12, discussed below. Sensor array 26 may be disposed within a sensor array housing 29. Sensor array housing 29 may be composed of any suitable non-ferrous material such as plastic, ceramic, and the like. In embodiments, sensor array 26 may be disposed in a fluid within sensor array housing 29. This may prevent sensor array 26 from moving during operations and further protect sensor array 26 from subsurface pressure. Sensor array 26 may be disposed at any suitable location within housing 20. Such disposing may be at about the top, about the bottom, or about the center of housing 20. Additionally, there may be a plurality of sensor arrays 26 disposed throughout housing 20. As illustrated in FIG. 2, sensory array 26 may comprise at least one receiving coil array 32, at least one ferri-core 30, and at least one transmitter coil 34. In embodiments, receiving coil array 32 may comprise any suitable material. Suitable material may be, but is not limited to, aluminum, copper, nickel, steel, and/or any combination thereof. Receiving coil array 32 may be any suitable length. A suitable length may be, but is not limited to, about one inch to about three inches, about two inches to about four inches, about three inches to about six inches, about four inches to about eight inches, about five inches to about ten inches, or about six inches to about twelve inches. Receiving coil array 32 may be longer than ferri-core 30. Receiving coil array 32 may be any suitable shape. A suitable shape may be, but is not limited to, round, oval, square, triangular, polyhedral, and/or any combination thereof. Receiving coil array 32 may sense voltage from the emitted electro-magnetic field as originally transmitted by sensory array 26. Difference in the voltages measured from tubing 12 by at least one sensor array 26 may be used to identify characteristics of tubing 12. The electro-magnetic field may be transmitted, directed, and focused within a desired area by ferri-core 30.

Figure 3A:
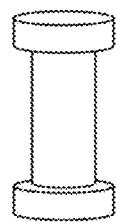
FIG. 3a illustrates an embodiment of a dumbbell-shaped core.
Figure 3B:
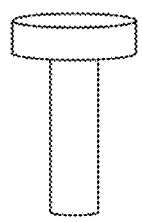
FIG. 3b illustrates an embodiment of a hammer-shaped core.
Figure 3C:
FIG. 3c illustrates an embodiment of a side tapered core.
Figure 3D:
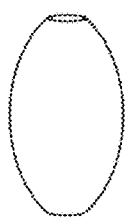
FIG. 3d illustrates an embodiment of a center tapered core.

Ferri-core 30, as illustrated in FIG. 2 may be a medium in which an electro-magnetic field is broadened, which may induce an eddy current within tubing 12. In embodiments, ferri-core 30 may comprise any suitable material. Suitable material may be, but is not limited to, ferrite, silicon steel, nickel steel, alloy powder core, and/or any combination thereof. Ferri-core 30 may be any suitable length. A suitable length may be, but is not limited to, about one inch to about three inches, about two inches to about four inches, about three inches to about six inches, about four inches to about eight inches, about five inches to about ten inches, or about six inches to about twelve inches. In embodiments, ferri-core 30 may be shorter than receiving coil array 32. Ferri-core 30 may be any suitable shape. A suitable shape may be, but is not limited to, round, oval, square, triangular, polyhedral, and/or any combination thereof. Additionally, ferri-core 30 may be configured in any suitable structure in which to transmit an electro-magnetic field to and through tubing 12. As illustrated in FIGS. 3a-3d, structures of ferri-core 30 may vary. Specifically, a configuration may be dumbbell-shaped (FIG. 3a), hammer-shaped (FIG. 3b), side tapered (FIG. 3c), and/or center tapered (FIG. 3d). Each configuration may produce a different type of electro-magnetic field. For example, a dumbbell-shaped ferri-core 30 may focus and/or guide the electro-magnetic field horizontally to a desired depth. A hammer-shaped ferri-core 30 may block magnetic interference from an end of ferri-core 30. A tapered shaped ferri-core 30 may reduce motion noise. A center tapered ferri-core 30 may focus the electro-magnetic field about the center of ferri-core 30. In embodiments, ferri-core 30 may be a structure in which receiver coil array 32 and transmitter coil 34 may be disposed.

Transmitter coil 34, as illustrated in FIG. 2 may be a wire, which may be wound around all ferri-cores 30 and receiving coil array 32. In embodiments, transmitter coil 34 may comprise any suitable material. Suitable material may be, but is not limited to, aluminum, copper, nickel, steel, and/or any combination thereof. In embodiments, transmitter coil 34 may eliminate coupling power between transmitter coil 34 and receiving coil array 32. This may be accomplished as each ferri-core 30 may transmit magnetic flux with transmitter coil 34. The magnetic flux may be directed in the same direction due to each ferri-core 30, which may eliminate individual magnetic flux loops. Transmitter coil 34 may boost the power associated with the production of an electro-magnetic field. This may increase the distance in which the electro-magnetic field may extend from sensor array 26.

During operation, transmitter coil 34 may be energized to produce an electro-magnetic field through ferri-core 30, which may induce an eddy current in tubing 12. Transmitter coil 34 may then be switched off, which may allow for receiving coil array 32 to record the voltage within tubing 12, as produced from the induced eddy current. A microprocessor and/or control unit may be used to direct current into and out of transmitter coil 34. Current may be used to energize transmitter coil 34, which may create an electro-magnetic field through ferri-core 30. Additionally, the microprocessor may be used to record and transmit the recorded voltages within receiving coil array 32.

An electro-magnetic field may be produced and emitted from sensor array 26. In embodiments, the electro-magnetic field may be strong and large enough to induce an eddy current in second tube 38. It should be noted that electro-magnetic field may induce an eddy current in additional outside tubing. Electro-magnetic field may be directed by ferri-core 30. As discussed above, different configurations of ferri-core 30 may direct electro-magnetic field differently, which may be selected by the operator. In embodiments, transmitter coil 34 may be turned off and on at any given length of time. When turned on, the transmitter coil 34 may produce an electro-magnetic field, which may be directed by ferri-core 30 and induce eddy current in tubing 12. Transmitter coil 34 may then be switched off, which may allow for receiving coil array 32 to sense and record the voltage produced by the induced eddy current. Turning transmitter coil 34 on and off may be repeated continuously as measurements of tube 12 are performed.

Measurements, inspections, and detection may take place as inspection device 4 moves through tube 12 in any direction. Travel time of inspection device 4 through a zone of interest within tube 12 may depend on the duration of pulses and amplitude used to produce and transmit an electro-magnetic field through inspection device 4. Duration of a pulse may be set so that the signal variation between the excitation time and the "infinite" excitation time may be less than the noise constantly detected at signal level. Duration may vary based on the "electromagnetic" wall thickness of the inspected tube 12. Electromagnetic wall thickness refers to the given conductivity and relative permeability with tube 12 thickness. The electro-magnetic field created by the pulse may be used to induce an eddy current in tube 12 and/or additional tubing. Additionally, ferri-cores 30 may allow for inspection device 4 to transmit an electro-magnetic field three hundred and sixty degrees, which may allow inspection device 4 to inspect the entirety of tube 12, surrounding tubes, and/or casing 14.

In embodiments, signals recorded by receiving coil array 32 may be processed using information handling system 40. Referring to FIG. 1, information handling system 40 may be disposed within inspection device 4 at any location. Without limitation, information handling system 40 may also be disposed on the surface within service device 10. Processing may take place within information handling system 40 within inspection device 4 and/or on the surface in service device 10. Information handling system 40 within inspection device 4 may connect to service device 10 through waveguide 43, which may be disposed within tether 16. It is to be understood that waveguide 43 is shown as disposed in FIG. 1 for illustration purposes only as it is disposed within tether 16. Information handling system 40 may act as a data acquisition system and possibly a data processing system that analyzes signals from receiving coil array 32, for example, to derive one or more properties of tubing 12.

Without limitation in this disclosure, information handling system 40 may include any instrumentality or aggregate of instrumentalities operable to compute, classify, process, transmit, receive, retrieve, originate, switch, store, display, manifest, detect, record, reproduce, handle, or utilize any form of information, intelligence, or data for business, scientific, control, or other purposes. For example, information handling system 40 may be a personal computer, a network storage device, or any other suitable device and may vary in size, shape, performance, functionality, and price. Information handling system 40 may include random access memory (RAM), one or more processing resources such as a central processing unit (CPU) or hardware or software control logic, ROM, and/or other types of nonvolatile memory. Additional components of information handling system 40 may include one or more disk drives, one or more network ports for communication with external devices as well as various input and output (I/O) devices, such as a keyboard, a mouse, and a video display. Information handling system 40 may also include one or more buses operable to transmit communications between the various hardware components.

Certain examples of the present disclosure may be implemented at least in part with non-transitory computer-readable media. For the purposes of this disclosure, non-transitory computer-readable media may include any instrumentality or aggregation of instrumentalities that may retain data and/or instructions for a period of time. Non-transitory computer-readable media may include, for example, without limitation, storage media such as a direct access storage device (e.g., a hard disk drive or floppy disk drive), a sequential access storage device (e.g., a tape disk drive), compact disk, CD-ROM, DVD, RAM, ROM, electrically erasable programmable read-only memory (EEPROM), and/or flash memory; as well as communications media such wires, optical fibers, microwaves, radio waves, and other electromagnetic and/or optical carriers; and/or any combination of the foregoing.

Figure 4:
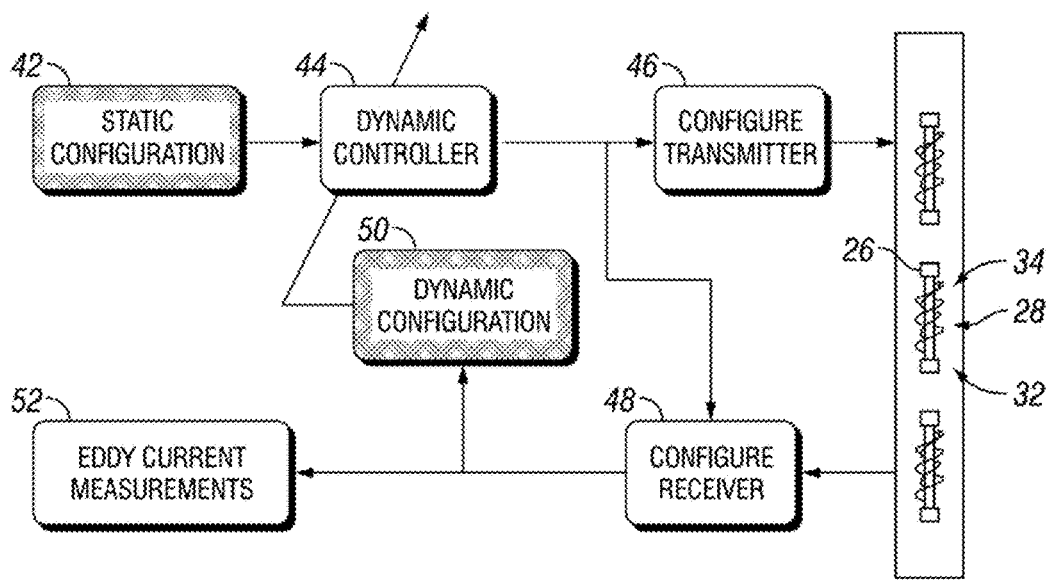
FIG. 4 illustrates a schematic for dynamic control.

Information handling system 40 may dynamically control sensor array 26 based on the conditions experienced by inspection device 4. FIG. 4 illustrates a system diagram of the dynamic controls information handling system 40 may perform during operation. During operation, information handling system 40 may first operate sensor array 26 in a static configuration 42. Static configuration 42 may be described as the initial configuration of sensor array 26 based on known requirements and the environment inspection device 4 may experience within tubing 12. It should be noted that there may be one or more initial configurations, which may be selected based on time and/or location of information handling system 40. Static configuration 42 may be fed to dynamic controller 44, which may be a component of information handling system 40. Dynamic controller 44 may then alter transmitter coil 34, illustrated in the flow chart as item 46. Configuration of transmitter coil 34 may alter the amplitude and phase of an emitted magnetic field from transmitter coil 34. As described above, different configurations (Referring to FIGS. 3a-3d) may affect the emitted magnetic field in different ways. Additionally, dynamic controller 44 may configure receiving coil array 32, illustrated in flow chart as item 48, to record signals and electromagnetic fields produced by tubing 12. During operation, the movement of inspection device 4 and the requested detail of recording by receiving coil array 32 may include changing static configuration 42. Dynamic configuration 50 may take the information as to the movement of inspection device 4 and receiving coil array 32 recording requirements into consideration to alter the configuration of transmitter coil 34, and receiving coil array 32. Desired alteration may be sent to dynamic controller 44, which may re-configure transmitter coil 34 and receiving coil array 32 during operation. This may result in more accurate and detailed eddy current measurements 52.

Dynamic configuration 50 of sensor array 26 may generate different apertures during operation to compensate for movement of inspection device 4 and downhole conditions. For example, dynamic configuration 50 may boost the signal from transmitter coil 34 as inspection device 4 is moving in one direction, compensate for motion jitters of inspection device 4 which may create unwanted noise, select different types of apertures based on preferred resolution of the aperture and inspection device 4 speed, gain control of aperture for different detection depth, and phase control of transmitter coil 34 for focusing effect. During operation, an induced eddy current in tubing 12 may decay gradually with time. An electromagnetic field recorded by receiving coil array 32 may be interpreted as a received voltage, which may be an integral of the receiver transfer function and eddy current distribution as illustrated in Equation 1 below.

$$V_{(z,t)} = K \cdot \int H(z - (z' + \Delta z_{noi(t)})) \cdot J(z',t) dz' \quad (1)$$

Within Equation 1, V(z,t) is the voltage reading on receiving coil array 32 at depth z on time t. K is the coefficient of the linear equation. H(z) is the receiving transfer function at depth z, as the tool is moving during the acquisition $\Delta z_{noi(t)}$ is the motion noise. During operation, motion noise may be used within Equation (1) during the final voltage reading on receiving coil array 32, identified as V(z,t). J(z,t) is the eddy current distribution in the pipe at time t. The original eddy current space distribution may be determined by the transmitter aperture.

Figure 5:
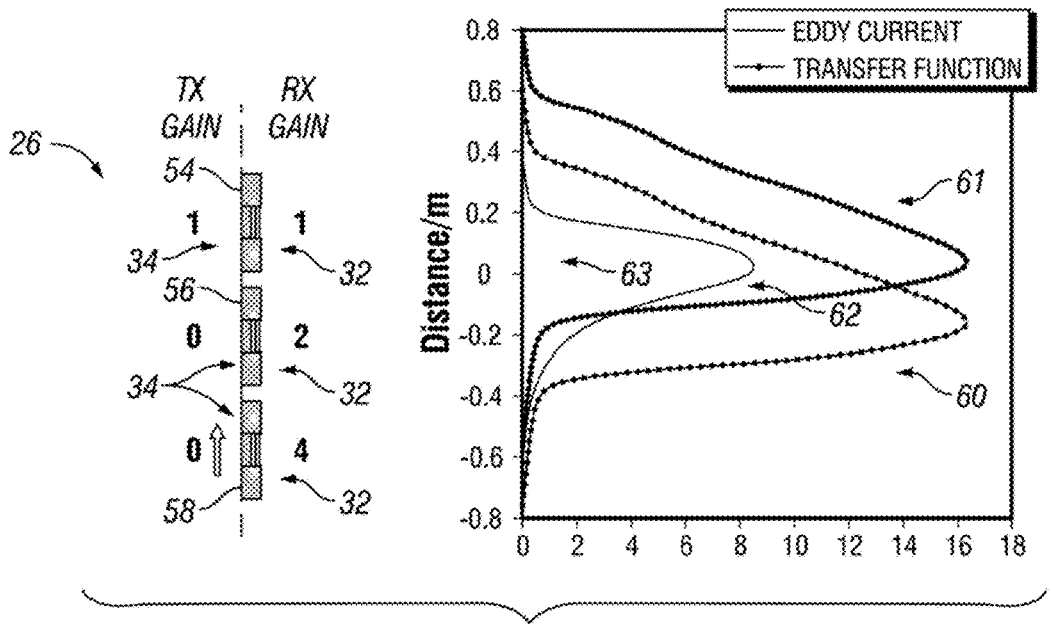
FIG. 5 illustrates an example of dynamic control of sensor arrays.

As illustrated, in FIG. 5, inspection tool 4 is moving in one direction. In embodiments, dynamic configuration 50 may gradually increase receiving aperture 60 as inspection tool 4 moves in one direction. In examples, an inspection tool 4 may comprise a first sensor array 54, a second sensor array 56, and a third sensor array 58. Each sensor array may comprise a transmitter coil 34 and/or receiver coil array 32. The eddy current induced by ferri core 30, transmitter coil 34, may be decaying gradually and may hold a constant position within tubing 12. Thus, the recorded signal may remain at the same level at different times. Inspection tool 4, as illustrated in FIG. 5, is moving in an upward motion. Transmitter coil 34 may be energized, denoted as a gain of 1, to produce an eddy current in a first sensor array 54. Gain may be defined as the measurement of the amount of energy within transmitter coil 34 and/or receiving coil array 32. As illustrated, second sensor array 56 and third sensor array 58 may not have energized their respective transmitter coil 34. Sensing the constant movement in a single direction, dynamic configuration 50 increases the gain for receiving coil array 32 at first sensor array 54, second sensor array 56, and third sensor array 58. As discussed above, the eddy current produced by transmitter coil 34 in first sensor array 54 may be decaying gradually and may hold a constant position. The graph in FIG. 5 illustrates induced eddy current 62 within tubing 12. Without limitation, to record induced eddy current 62, receiving coil array 32 on first sensor array 54 may be energized with a gain of 1, second sensor array 56 may be energized with a gain of 2, and third sensor array 58 may be energized with a gain of 4. It should be noted that the gain of any receiving coil array 32 may be altered for any conditions downhole. Energizing receiving coil array 32 on first sensor array 54, second sensor array 56, and third sensor array 58 may produce aperture 60. Aperture may be defined as the recording and sensor area of receiving coil array 32 on first sensor array 54 and/or in combination with second sensor array 56 and/or third sensor array 58. As illustrated, aperture 60 may enclose, thus sense and record, induced eddy current 62. As inspection tool 4 continues to move to a second point in time, induced eddy current 62 may have degraded to second induced eddy current 63. Additionally, aperture 60 may have moved up with inspection tool 4 as illustrated by second aperture 61. Thus, the integration of induced eddy current 62 and aperture 60 may remain in the same area as the integration of second induced eddy current 63 and second aperture 61. This may improve the signal to noise ratio recorded by sensory arrays 26, which may prevent the loss and/or skewing of data.

Figure 6A:
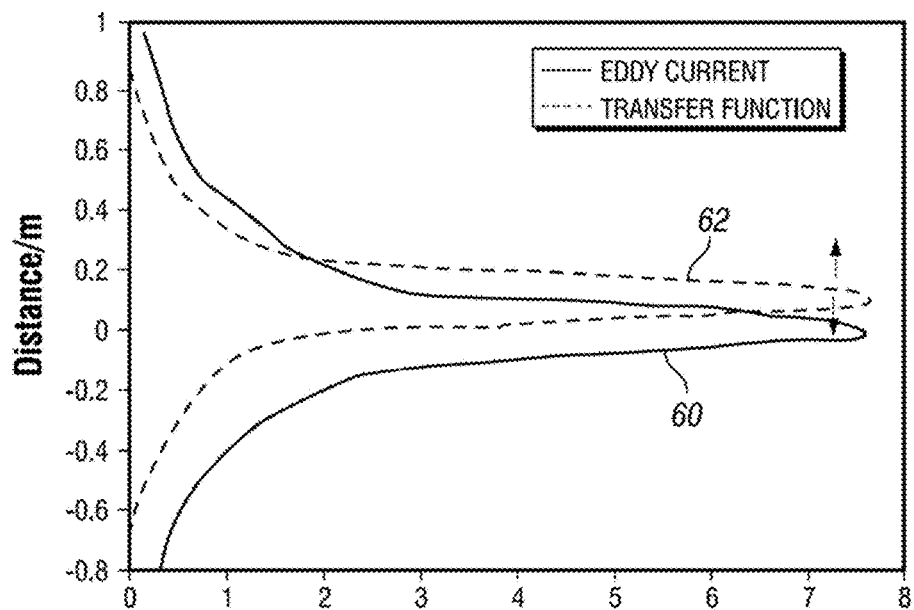
FIG. 6a illustrates noise created from an inspection device sporadic movement.
Figure 6B:
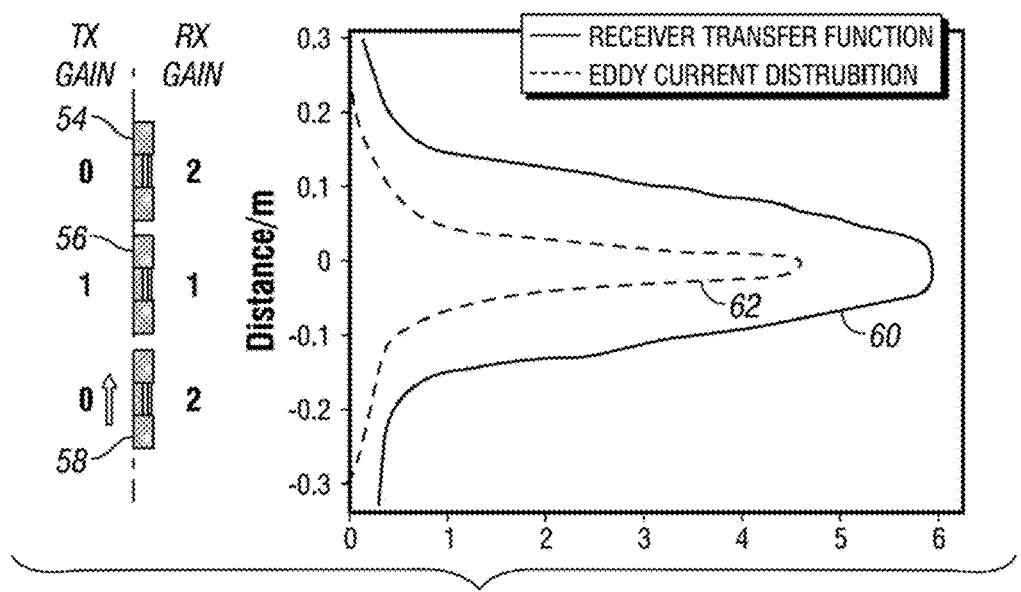
FIG. 6b illustrates dynamic control to prevent noise from sporadic movement of the inspection device.

Dynamic configuration 50, as illustrated in FIGS. 6a and 6b, may configure sensor array 26 to compensate for motion noise. During operation, inspection tool 4 may not move uniformly, aperture 60 may shake along with inspection tool 4, where induced eddy current 62 may not move. Referring to FIG. 6a, this may create motion noise, as aperture 60 may move up and down sporadically, preventing receiving coil array 32 from recording the entire signal produced by induced eddy current 62, which is stationary. Dynamic configuration 50 may "flatten" and expand aperture 60, as illustrated in FIG. 6b. This may be accomplished by increasing the gain on first sensor array 56 and third sensor array 58, which may taper and expand the aperture. Without limitation, induced eddy current 62 may be recorded in its entirety even as aperture 60 may move up and down sporadically.

Figure 7:
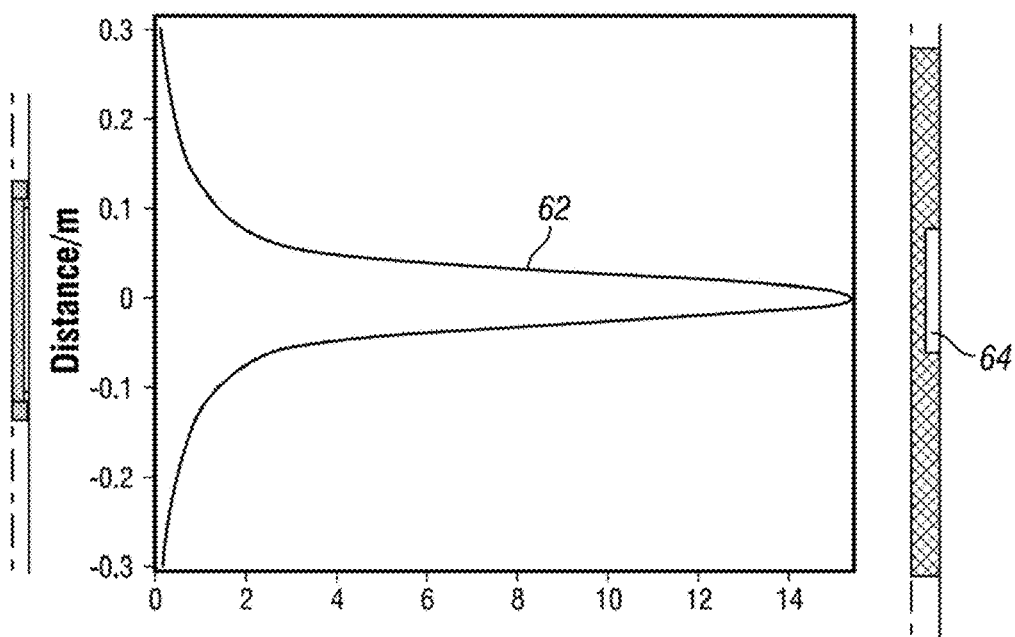
FIG. 7 illustrates an aperture to identify a target feature.
Figure 8A:
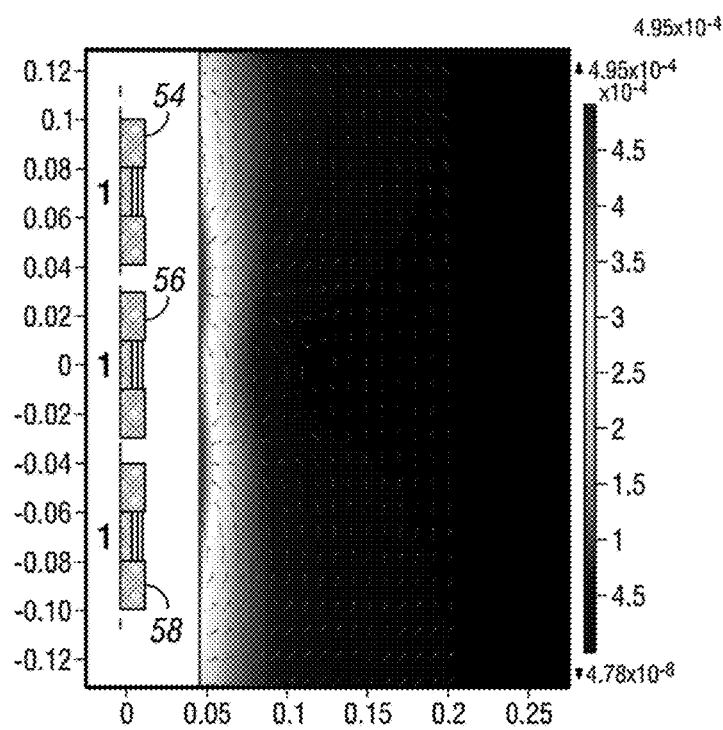
FIG. 8a illustrates an electric field produced by a first sensor array, a second sensor array, and a third sensor array.
Figure 8B:
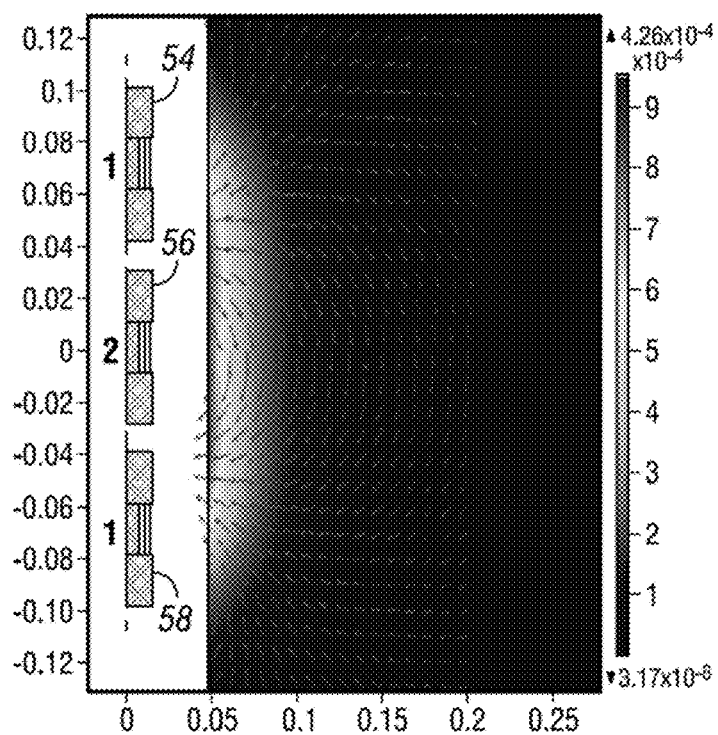
FIG. 8b illustrates another electric field produced by a first sensor array, a second sensor array, and a third sensor array.
Figure 8C:
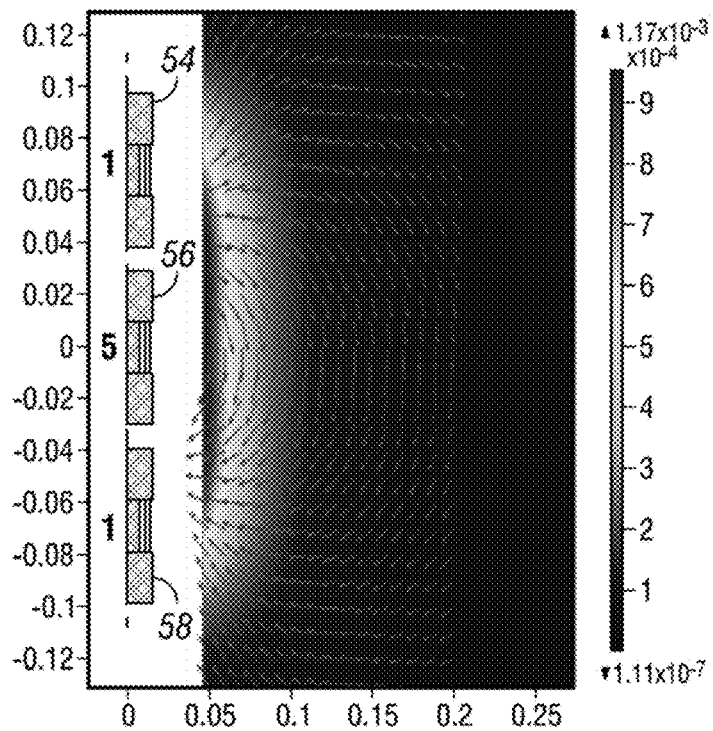
FIG. 8c illustrates another electric field produced by a first sensor array, a second sensor array, and a third sensor array.
Figure 8D:
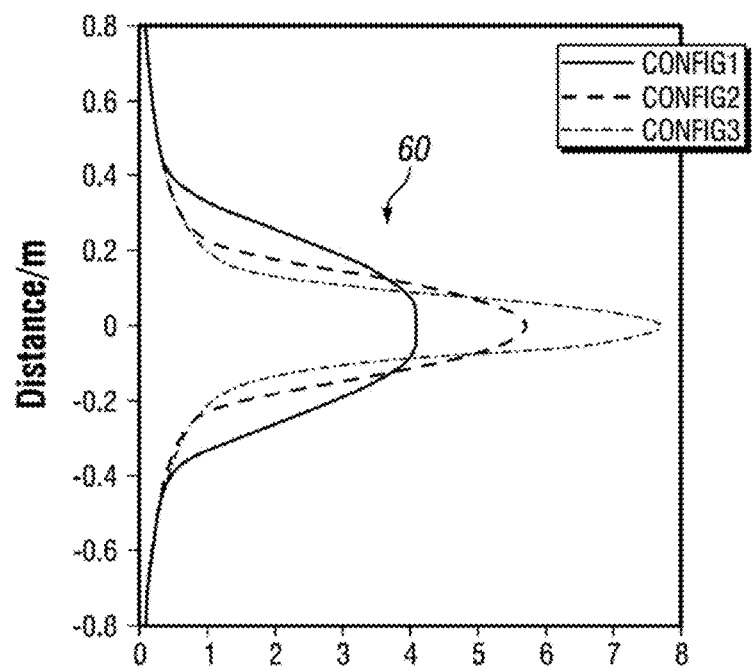
FIG. 8d illustrates apertures created from sensor arrays in FIGS. 8a, 8b, and 8c.

During operation, dynamic configuration 50 may further configure transmitter coil 34 during operation, which may control the resolution receiving coil array 32 may be able to record. As illustrated in FIG. 7, transmitter coil 34 may produce induced eddy current 62, through an electric field, that may be smaller than target feature 64 to be able to detect target feature 64. Thus, an induced eddy current 62 larger than target feature 64 may not have high enough resolution for receiving coil array 32 to record target feature 64. Dynamic configuration 50 may be able to adjust the number of transmitter coils 34 used and the speed of inspection tool 4 to increase and/or decrease the resolution recorded by receiving coil array 32. Without limitation, high resolution may be needed in harsh environments and older pipes in order to detect smaller target features 64, in which dynamic configuration 50 may shrink the electric field emitted from transmitter coil 34 and reduce the speed of inspection device 4. In areas near the surface with tubing 12 in a clean environment, a higher inspection tool 4 speed may be utilized by the operator, which may increase the size of the electric filed but reduce the resolution. FIGS. 8a-8d illustrate the electric fields produced by transmitter coils 34 and resolution produced by each one. Referring to FIG. 8a, first sensor array 54, second sensor array 56, and a third sensor array 58 are emitting the same electric field with the same amount gain for each transmitter coil. FIG. 8d illustrates that if first sensor array 54, second sensor array 56, and third sensor array 58 have the same gain, aperture 60 may be flattened and widened, which may produce low resolution. Referring to FIG. 8b, second sensor array 56 may produce a strong electric field due to an increase in gain in comparison to first sensor array 54 and third sensor array 58. FIG. 8d illustrates that if second sensor array 56 has an increased gain, aperture 60 produced may be thinner and longer than that produced by the arrangement in FIG. 8a. Referring to FIG. 8c, second sensor array 56 has a gain that has increased many times more than first sensor array 54 and third sensor array 58, which may produce a high resolution aperture as illustrated in FIG. 8*d*. The high resolution aperture may be longer and thinner than the previous apertures produced by FIGS. 8*a* and 8*b*.

Figure 9:
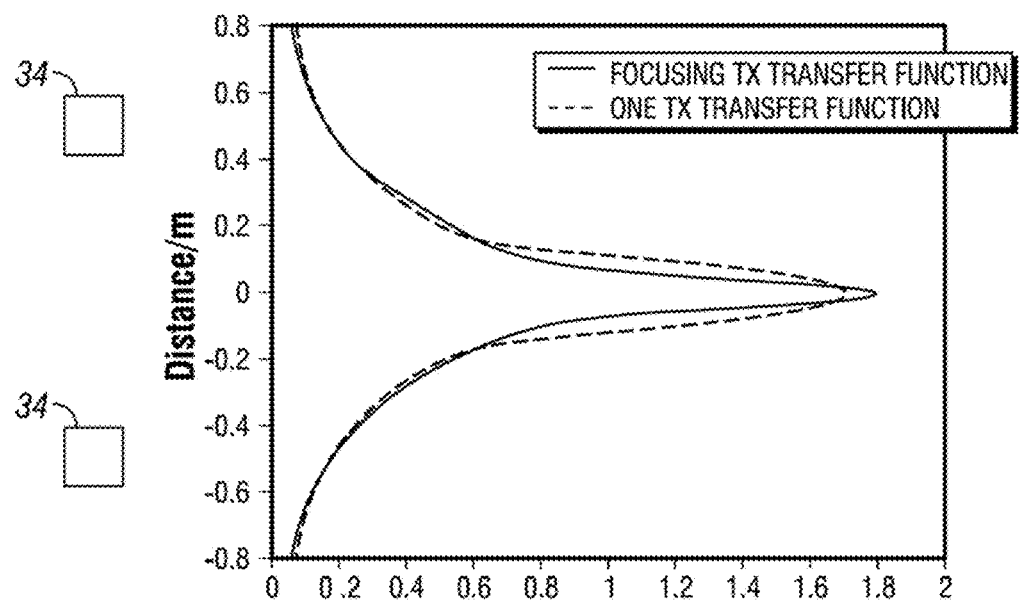
FIG. 9 illustrates an aperture created through phase shifting.

Without limitation, aperture 60 produced by transmitter coils 34 may be narrowed and increased in length using phase control, as illustrated in FIG. 9. In examples, aperture 60 transmitted by transmitter coil 34 may be limited by sensor size. By controlling current course of two transmitter coils 34 in one hundred eighty degree phase shifts, the flux of the electric fields may be focused between the two transmitter coils 34, which may increase and narrow aperture 60. This may help in detecting smaller target features 64 in tubing 12.

The preceding description provides various embodiments of the systems and methods of use disclosed herein which may contain different method steps and alternative combinations of components. It should be understood that, although individual embodiments may be discussed herein, the present disclosure covers all combinations of the disclosed embodiments, including, without limitation, the different component combinations, method step combinations, and properties of the system. It should be understood that the compositions and methods are described in terms of "comprising," "containing," or "including" various components or steps, the compositions and methods can also "consist essentially of" or "consist of" the various components and steps. Moreover, the indefinite articles "a" or "an," as used in the claims, are defined herein to mean one or more than one of the element that it introduces.

For the sake of brevity, only certain ranges are explicitly disclosed herein. However, ranges from any lower limit may be combined with any upper limit to recite a range not explicitly recited, as well as, ranges from any lower limit may be combined with any other lower limit to recite a range not explicitly recited, in the same way, ranges from any upper limit may be combined with any other upper limit to recite a range not explicitly recited. Additionally, whenever a numerical range with a lower limit and an upper limit is disclosed, any number and any included range falling within the range are specifically disclosed. In particular, every range of values (of the form, "from about a to about b," or, equivalently, "from approximately a to b," or, equivalently, "from approximately a-b") disclosed herein is to be understood to set forth every number and range encompassed within the broader range of values even if not explicitly recited. Thus, every point or individual value may serve as its own lower or upper limit combined with any other point or individual value or any other lower or upper limit, to recite a range not explicitly recited.

Therefore, the present embodiments are well adapted to attain the ends and advantages mentioned as well as those that are inherent therein. The particular embodiments disclosed above are illustrative only, and may be modified and practiced in different but equivalent manners apparent to those skilled in the art having the benefit of the teachings herein. Although individual embodiments are discussed, the disclosure covers all combinations of all of the embodiments. Furthermore, no limitations are intended to the details of construction or design herein shown, other than as described in the claims below. Also, the terms in the claims have their plain, ordinary meaning unless otherwise explicitly and clearly defined by the patentee. It is therefore evident that the particular illustrative embodiments disclosed above may be altered or modified and all such variations are considered within the scope and spirit of those embodiments. If there is any conflict in the usages of a word or term in this specification and one or more patent(s) or other documents that may be incorporated herein by reference, the definitions that are consistent with this specification should be adopted Although the present invention and its advantages have been described in detail, it should be understood that various changes, substitutions alterations may be made herein without departing from the spirit and scope of the invention as defined by the appended claims.

The invention claimed is:

1. A method of creating a synthetic aperture comprising:
disposing an inspection device into a tubing;
identifying a static configuration;
inputting the static configuration into a dynamic controller;
configuring a transmitter disposed on the inspection device with the dynamic controller;
inducing an eddy current in the tubing with the transmitter;
configuring a receiver on the inspection device with the dynamic controller;
recording the eddy current in the tubing with the receiver;
inputting operational variables and environmental variables into a dynamic configuration;
inputting the dynamic configuration into the dynamic controller;
re-configuring the transmitter and the receiver with the dynamic controller;
generating a plurality of apertures during operation to compensate for movement of the inspection device and downhole conditions, wherein the plurality of apertures enclose, sense, and record the eddy current; and
changing an aperture with the dynamic controller.

2. The method of claim 1, further comprising:
a telemetry module, wherein the telemetry module comprises an accelerometer;
a centralizing module, wherein the centralizing module comprises at least three arms;
an inspection device, wherein the inspection device comprises a memory module, a transmitter and receiver controller, and a sensor array, wherein the sensor array comprises a receiving coil array, a ferri-core, and a transmitter coil; and
a service device.

3. The method of claim 2, wherein the ferri-core is constructed in a dumbbell-shape, a hammer-shape, a tapered-shape, or a center tapered-shape.

4. The method of claim 2, further comprising a plurality of sensor arrays.

5. The method of claim 2, further comprising at least one transmitter coil wound around at least a part of the ferri-core.

6. The method of claim 2, further comprising at least one receiver coil wound around at least a part of the ferri-core.

7. The method of claim 1, further comprising detecting an inspection tool moving in a single direction and maintaining a prescribed signal to noise ratio.

8. The method of claim 7, further comprising maintaining gain on a first sensor array, increasing gain on a second sensor array, and increasing gain on a third sensor array above the gain of the second sensor array.

9. The method of claim 1, further comprising detecting sporadic movement of an inspection device and compensation for the sporadic movement.

10. The method of claim 9, further comprising maintaining gain on a second sensor array and increasing gain on a first sensor array and a third sensor array.

11. The method of claim 1, further comprising detecting a downhole environment in which an inspection tool is traversing.

12. The method of claim 11, further comprising detecting a harsh environment and increasing gain on a transmitter and slowing a speed of the inspection tool.

13. The method of claim 11, further comprising detecting a clean environment and lowering gain on a transmitter and increasing speed on the inspection tool.

14. The method of claim 1, further comprising increasing depth and resolution of a transmitter aperture by increasing gain on a second sensor array.

15. The method claim 1, further comprising increasing depth and resolution of a transmitter aperture by controlling current source of a first transmitter and a second transmitter in a one hundred and eighty degree phase shift.

* * * * *